US00PP20870P2

(12) United States Plant Patent
Dümmen

(10) Patent No.: US PP20,870 P2
(45) Date of Patent: Mar. 23, 2010

(54) ***PETUNIA* PLANT NAMED 'DUESURIMWI'**

(50) Latin Name: *Petunia×hybrida*
Varietal Denomination: Duesurimwi

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/316,457

(22) Filed: Dec. 12, 2008

(51) Int. Cl.
*A01H 5/00* (2006.01)

(52) U.S. Cl. ..... Plt./356

(58) Field of Classification Search ..... Plt./356
See application file for complete search history.

(56) References Cited

U.S. PATENT DOCUMENTS

PP15,122 P2 * 8/2004 Heffner ..... Plt./356

OTHER PUBLICATIONS

UPOV ROM GTITM Computer Database, GTI Jouve Retrieval Software 2009/03 Citation for 'Duesurimwi'.*

* cited by examiner

*Primary Examiner*—Wendy C Haas
(74) *Attorney, Agent, or Firm*—C. A. Whealy

(57) ABSTRACT

A new and distinct cultivar of *Petunia* plant named 'Duesurimwi', characterized by its outwardly spreading to trailing growth habit; freely branching habit; early and freely flowering habit; white-colored flowers; and good garden performance.

1 Drawing Sheet

Botanical designation: *Petunia×hybrida.*
Cultivar denomination: 'DUESURIMWI'.

CROSS-REFERENCED TO CLOSELY RELATED APPLICATIONS

U.S. Plant patent application Ser. No. 12/316,476.

BACKGROUND OF THE INVENTION

The present invention relates to a new and distinct cultivar of *Petunia* plant, botanically known as *Petunia×hybrida* and hereinafter referred to by the name 'Duesurimwi'.

The new *Petunia* plant is a product of a planned breeding program conducted by the Inventor in Rheinberg, Germany. The objective of the breeding program is to create new trailing *Petunia* cultivars with numerous attractive flowers.

The new *Petunia* plant originated from a cross-pollination made by the Inventor in August, 2005 in Rheinberg, Germany of a proprietary selection of *Petunia×hybrida* identified as code number T04-0063-008, not patented, as the female, or seed, parent with a proprietary selection of *Petunia×hybrida* identified as code number F-19-18, not patented, as the male, or pollen, parent. The new *Petunia* was discovered and selected by the Inventor as a single flowering plant within the progeny of the stated cross-pollination in a controlled greenhouse environment in Rheinberg, Germany in May, 2007.

Asexual reproduction of the new *Petunia* plant by terminal cuttings in a controlled greenhouse environment in Rheinberg, Germany since May, 2007, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duesurimwi'. These characteristics in combination distinguish 'Duesurimwi' as a new and distinct cultivar of *Petunia:*

1. Outwardly spreading to trailing growth habit.
2. Freely branching habit.
3. Early and freely flowering habit.
4. White-colored flowers.
5. Good garden performance.

Plants of the new *Petunia* can be compared to plants of the female parent selection. Plants of the new *Petunia* differ primarily from plants of the female parent selection in flower color.

Plants of the new *Petunia* can be compared to plants of the male parent selection. Plants of the new *Petunia* differ primarily from plants of the male parent selection in flower color.

Plants of the new *Petunia* differ primarily from plants of *Petunia×hybrida* 'Duesurwice', disclosed in U.S. Plant patent application Ser. No. 12/316,476, in flower color as plants of 'Duesurwice' have pale pink-colored flowers with purple-colored venation.

Plants of the new *Petunia* can be compared to plants of the *Petunia×hybrida* 'Famous Snow White', not patented. In side-by-side comparisons conducted in Rheinberg, Germany, plants of the new *Petunia* differed primarily from plants of 'Famous Snow White' in the following characteristics:

1. Plants of the new *Petunia* were more compact than plants of 'Famous Snow White'.
2. Plants of the new *Petunia* had larger leaves than plants of 'Famous Snow White'.
3. Plants of the new *Petunia* had smaller flowers with shorter peduncles than plants of 'Famous Snow White'.

BRIEF DESCRIPTION OF THE PHOTOGRAPH

The accompanying colored photograph illustrates the overall appearance of the new *Petunia*, showing the colors as true as it is reasonably possible to obtain in colored reproductions of this type. Colors in the photograph may differ slightly from the color values cited in the detailed botanical description which accurately describe the colors of the new *Petunia* plant. The photograph comprises a close-up view of typical flowers and leaves of 'Duesurimwi'.

DETAILED BOTANICAL DESCRIPTION

The aforementioned photograph and following observations, measurements and values describe plants grown in Rheinberg, Germany, under commercial practice during the spring in a glass-covered greenhouse with day and night temperatures averaging 18° C. and light levels averaging 4,500 lux. Rooted young plants had been growing for 16 weeks when the photograph and description were taken. Plants were pinched one time about three weeks after planting. In the following description, color references are made to The Royal Horticultural Society Colour Chart, 2001 Edition, except where general terms of ordinary dictionary significance are used.

Botanical classification: *Petunia×hybrida* 'Duesurimwi'.

Parentage:

*Female, or seed, parent.*—Proprietary selection of *Petunia×hybrida* identified as code number T04-0063-008, not patented.

*Male, or pollen, parent.*—Proprietary selection of *Petunia×hybrida* identified as code number F19-18, not patented.

Propagation:

*Type.*—By terminal cuttings.

*Time to initiate roots, summer.*—About seven days at temperatures of 20° C.

*Time to initiate roots, winter.*—About ten days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching; dense.

Plant description:

*Plant and growth habit.*—Outwardly spreading to trailing growth habit. Freely branching habit with about eight to ten lateral branches developing after pinching. Moderately vigorous growth habit.

*Plant height.*—About 26 cm.

*Plant diameter.*—About 30 cm.

Lateral branch description:

*Length.*—About 25 cm.

*Diameter.*—About 4 mm.

*Internode length.*—About 2.7 cm.

*Strength.*—Moderately strong.

*Aspect.*—Initially upright to outwardly spreading.

*Texture.*—Pubescent.

*Color.*—Close to 144A to 144B.

Foliage description:

*Arrangement.*—Before flowering, alternate, simple; after flowering, opposite, simple.

*Length.*—About 5.7 cm.

Width: About 3.7 cm.

*Shape.*—Spatulate.

*Apex.*—Obtuse.

*Base.*—Attenuate.

*Margin.*—Entire.

*Texture, upper and lower surfaces.*—Pubescent; leathery.

*Venation pattern.*—Pinnate; arcuate.

*Color.*—Developing and fully expanded leaves, upper surface: Close to 137A; venation, close to 144B. Developing and fully expanded leaves, lower surface: Close to 137C; venation, close to 144B.

*Petiole length.*—About 6 mm.

*Petiole diameter.*—About 3 mm.

*Petiole texture, upper and lower surfaces.*—Pubescent.

*Petiole color, upper and lower surfaces.*—Close to 144B.

Flower description:

*Flower arrangement and habit.*—Salverform flowers; single flowers arising from leaf axils. Freely flowering habit with usually about 25 to 30 open flowers and flower buds per plant. Flowers face upright to outwardly.

*Fragrance.*—None detected.

*Natural flowering season.*—Plants flower continuously from late spring into autumn in Germany. Early flowering habit, plants typically beginning flowering about nine weeks after planting.

*Flower longevity.*—Individual flowers last about five days on the plant; flowers persistent.

*Flower diameter.*—About 5.5 cm.

*Flower length (height).*—About 2.6 cm.

*Flower throat diameter.*—About 1.1 cm.

*Flower tube diameter.*—About 2.5 mm.

*Flower bud.*—Shape: Ovoid. Length: About 3.9 cm. Diameter: About 6 mm. Color: Close to 155A.

*Corolla.*—Arrangement: Five petals fused at the base and opening into a flared trumpet. Petal length from throat: About 2.9 cm. Petal lobe width: About 2.7 cm. Petal shape: Roughly spatulate. Petal apex: Rounded. Petal margin: Entire. Petal texture, upper and lower surfaces: Smooth, glabrous; satiny. Throat texture: Smooth, glabrous. Tube texture: Pubescent. Color: Petal, when opening and fully opened, upper surface: Close to 155C, color does not fade with development; venation, close to 144B. Petal, when opening and fully opened, lower surface: Close to 155B; venation, close to 144B. Flower throat: Close to 144B; venation, close to 60B. Flower tube: Close to 144B; venation, close to 144B.

*Calyx.*—Arrangement: One star-shaped calyx tube with five sepals fused at the base per flower. Sepal length: About 3 cm. Sepal width: About 5 mm. Sepal shape: Narrowly oblong. Sepal apex: Rounded. Sepal margin: Entire. Sepal texture, upper and lower surfaces: Pubescent. Color, immature and mature, upper surface: Close to 137A. Color, immature and mature, lower surface: Close to 137C.

*Peduncles.*—Length: About 2 cm. Diameter: About 2 mm. Strength: Moderately strong. Texture: Pubescent. Color: Close to 144B.

*Reproductive organs.*—Stamens: Quantity/arrangement: Five per flower. Anther shape: Ovate. Anther length: About 2.5 mm. Anther color: Close to 2D. Pollen amount: Abundant. Pollen color: Close to 2D. Pistils: Quantity: One per flower. Pistil length: About 2.5 cm. Style length: About 1.9 cm. Style color: Close to 145B. Stigma shape: Rounded. Stigma color: Close to 144B. Ovary color: Close to 144B. Seed/fruit: Seed and fruit development have not been observed on plants of the new *Petunia*.

Garden performance: Plants of the new *Petunia* have been observed to have good garden performance and tolerate wind, rain and temperatures ranging from about 2° C. to about 38° C.

Pathogen/pest resistance: Plants of the new *Petunia* have not been observed to be resistant to pathogens and pests common to *Petunia*.

It is claimed:

1. A new and distinct *Petunia* plant named 'Duesurimwi' as illustrated and described.

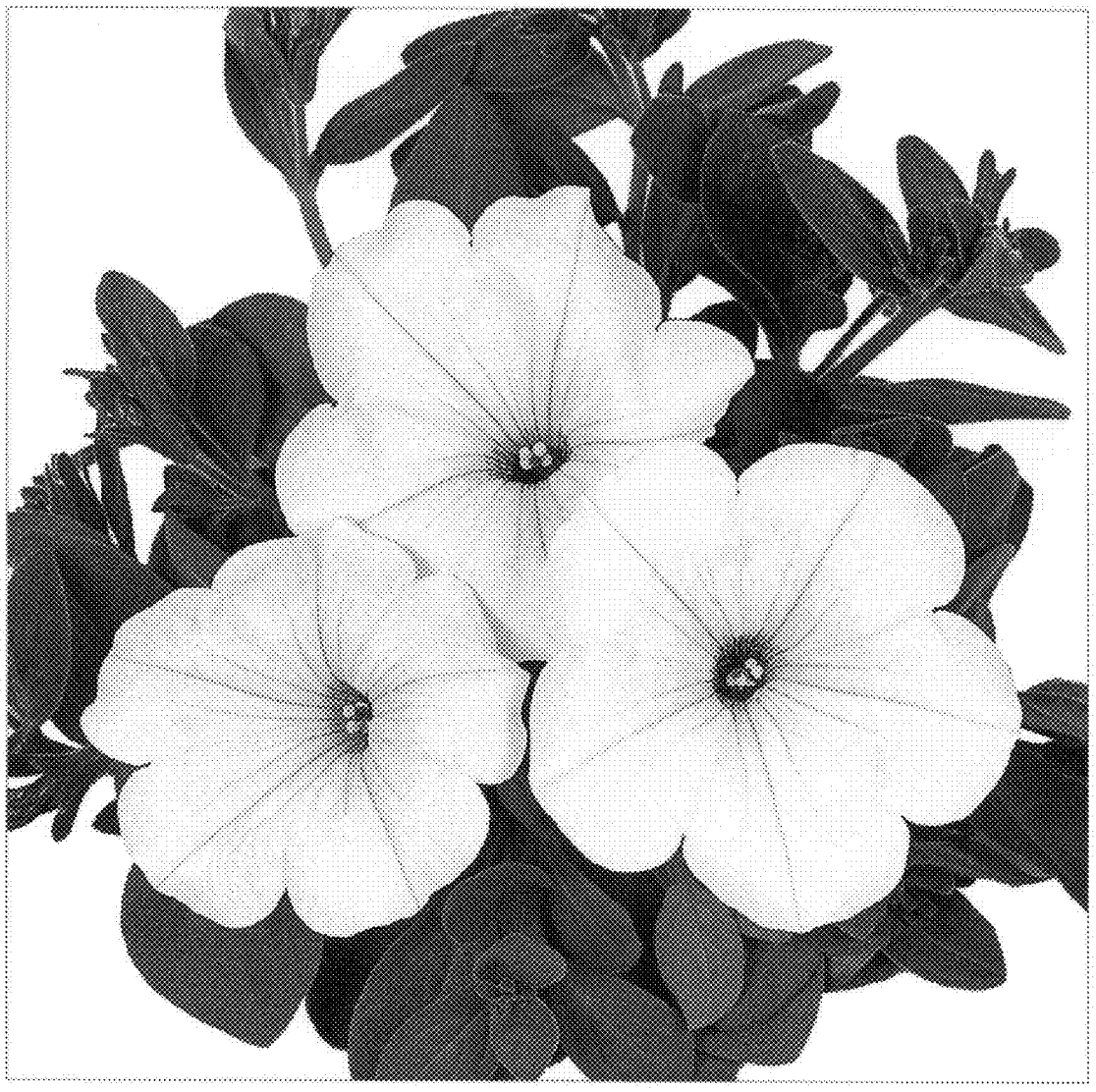

* * * * *